(12) United States Patent
Parry et al.

(10) Patent No.: US 12,359,225 B2
(45) Date of Patent: Jul. 15, 2025

(54) SYSTEM AND METHODS FOR IMPROVED ANAEROBIC DIGESTION

(71) Applicant: JACOBS ENGINEERING GROUP, INC., Dallas, TX (US)

(72) Inventors: David Lloyd Parry, Heber City, UT (US); Ester Rus Perez, Dallas, TX (US)

(73) Assignee: Jacobs Engineering Group, Inc., Dallas, TX (US)

( * ) Notice: Subject to any disclaimer, the term of this patent is extended or adjusted under 35 U.S.C. 154(b) by 140 days.

(21) Appl. No.: 17/111,632

(22) Filed: Dec. 4, 2020

(65) Prior Publication Data

US 2021/0171986 A1    Jun. 10, 2021

Related U.S. Application Data

(60) Provisional application No. 62/944,966, filed on Dec. 6, 2019.

(51) Int. Cl.
 *C12P 5/02* (2006.01)
 *C12M 1/107* (2006.01)

(52) U.S. Cl.
 CPC ............. *C12P 5/023* (2013.01); *C12M 21/04* (2013.01)

(58) Field of Classification Search
 CPC ................................ C12P 5/023; C12M 21/04
 See application file for complete search history.

(56) References Cited

U.S. PATENT DOCUMENTS

| 5,269,634 A | * | 12/1993 | Chynoweth | ............ | C05F 17/10 |
| | | | | | 405/129.25 |
| 2003/0094410 A1 | * | 5/2003 | Fassbender | ............ | C12M 23/34 |
| | | | | | 210/603 |
| 2010/0311140 A1 | | 12/2010 | Yanase et al. | | |

(Continued)

FOREIGN PATENT DOCUMENTS

| CN | 102583933 A | * | 7/2012 |
| EP | 3162898 A1 | * | 5/2017 |

OTHER PUBLICATIONS

Mulat et al. "Enhancing Methane Production from Lignocellulosic Biomass by Combined Steam-Explosion Pretreatment and Bioaugmentation with Cellulolytic Bacterium Caldicellulosiruptor bescil," Biotechnology for Biofuels, Jan. 29, 2018, vol. 11, No. 19, pp. 1-15.

(Continued)

*Primary Examiner* — Latosha Hines
(74) *Attorney, Agent, or Firm* — Dorsey & Whitney LLP

(57) ABSTRACT

The present disclosure relates generally to systems and methods for improving performance of anaerobic digestion by post-anaerobic digestion processing. The post-anaerobic digestion processing includes introducing a digestate to post-anaerobic digestion microorganisms downstream of an anaerobic digestion process, wherein the digestate is a product of anaerobic digestion and the post-anaerobic digestion microorganisms hydrolyze and ferment the digestate to produce hydrolysis and fermentation products. In some instances, the systems and methods further include introducing the hydrolysis and fermentation products to anaerobic digestion microorganisms, wherein the anaerobic digestion microorganisms convert the hydrolysis and fermentation products into biogas.

13 Claims, 5 Drawing Sheets

(56) References Cited

U.S. PATENT DOCUMENTS

2013/0210071 A1\* 8/2013 Mielenz .................. C12P 39/00
                                                                                            435/252.4
2016/0024603 A1    1/2016 Curvers et al.
2016/0160239 A1    6/2016 Hoff et al.

OTHER PUBLICATIONS

International Search Report and Written Opinion for International application No. PCT/US2020/063283, dated Mar. 11, 2021, 12 pages.

\* cited by examiner

SYSTEM AND METHODS FOR IMPROVED ANAEROBIC DIGESTION

CROSS REFERENCE TO RELATED APPLICATION

This application is a non-provisional of and claims the benefit of U.S. Application No. 62/944,966, entitled System and Methods for Improved Anaerobic Digestion, filed Dec. 6, 2019, which is hereby incorporated by reference in its entirety.

TECHNICAL FIELD

The technology described herein relates generally to anaerobic digestion, and more specifically to a post-digestion process for increasing organic conversion and biogas production produced by anaerobic digestion.

BACKGROUND

Anaerobic digestion is a process to stabilize and convert organic material into biogas. Biogas is composed of methane, carbon dioxide, water vapor, hydrogen sulfide, and small amounts of other compounds. The products of anaerobic digestion are biogas and biosolids. Bacteria and archaea microorganisms are responsible for three main stages of digestion: hydrolysis, fermentation (acidogenesis and acetogenesis), and methanogenesis (acetoclastic and hydrogenotrophic). In the hydrolysis stage, fats, carbohydrates, and proteins are hydrolyzed into fatty acids, sugars, and amino acids. In the fermentation stage, acidogenesis ferments the hydrolyzed products into smaller volatile fatty acids (VFAs) and alcohols. During acetogenesis, the VFAs are processed into smaller molecules such as acetic acid, hydrogen gas, and carbon dioxide. In the final methanogenesis stage, methane and carbon dioxide are formed from the small molecules by two microbial pathways: acetoclastic and hydrogenotrophic. Acetoclastic methanogens convert acetate into methane and carbon dioxide. Hydrogenotrophic methanogens use hydrogen for the reduction of carbon dioxide to methane and water.

The performance of anaerobic digestion has been improved by various processes. For example, anaerobic digestive performance has been improved by separation of the acid and gas phases and numerous other (biological, mechanical, thermal/chemical, and thermal) processes. However, certain materials are not hydrolyzed well or sufficiently in the currently known processes, producing limited biogas and increasing costs for handling or disposal of undigested biosolids.

The information included in this Background section of the specification, including any description or discussion thereof, is included for technical reference purposes only and is not to be regarded subject matter by which the scope of the invention as defined in the claims is to be bound.

SUMMARY

The technology disclosed herein is generally related to systems and methods that incorporate a post-anaerobic digestion process to increase organic conversion and biogas production resulting from anaerobic digestion.

In one embodiment, a post-anaerobic digestion process for increasing an amount of biogas produced during anaerobic digestion is disclosed. The process includes introducing a digestate to anaerobic microorganisms, wherein the digestate is a product of anaerobic digestion and the anaerobic microorganisms hydrolyze the digestate to produce hydrolysis products; and introducing the hydrolysis products to a second plurality of anaerobic microorganisms, wherein the second plurality of anaerobic microorganisms convert the hydrolysis products into biogas.

In one aspect, the digestate is a product of anaerobic digestion of feedstock. In one aspect, the first plurality of anaerobic microorganisms comprise thermophilic bacteria. In one aspect, the thermophilic bacteria comprise one or more bacteria selected from the genus *Caldicellulosiruptor*, *Clostridium thermocellum*, and *Thermoanaerobacterium saccharolyticum*. In one aspect, the thermophilic bacteria is *Caldicellulosiruptor bescii* (*C. bescii*). In one aspect, the process further includes allowing the first plurality of anaerobic microorganisms to hydrolyze one or more recalcitrant materials in the digestate. The one or more recalcitrant materials may be lignocellulosic. In one aspect, the process further includes storing the second plurality of anaerobic microorganisms in an environment having mesophilic or thermophilic temperatures.

In another embodiment, a method for converting organic material into biogas is disclosed. The method includes introducing organic material to a first anaerobic microbial community, wherein the first anaerobic microbial community converts the organic material into biogas and biosolids; feeding the biosolids to a second anaerobic microbial community, wherein the second anaerobic microbial community converts the biosolids into hydrolysis products; and introducing the hydrolysis products to the first anaerobic microbial community for conversion into additional biogas.

In one aspect, the method further includes pretreating the organic material with one or more pretreatment processes selected from biological hydrolysis, thermal hydrolysis, and a thermal/chemical pretreatment process. In one aspect, the second anaerobic microbial community includes *C. bescii*. In one aspect, the biosolids are the only food source and/or do not compete with other food sources for digestion by the *C. bescii*. In one aspect, the method further includes storing the second anaerobic microbial community in an environment having a thermophilic temperature and a neutral pH. In one aspect, the thermophilic temperature is between about 70° C.-80° C. In one aspect, the method further includes ammonia stripping of the hydrolysis products.

In yet another embodiment, a post-digestion treatment system for improving the performance of anaerobic digestion is disclosed. The system includes an anaerobic digester reactor (ADR) comprising a first population of anaerobic microbes; a hydrolysis/fermentation reactor (HFR) comprising second population of anaerobic microbes; and one or more fluid conduits coupling the ADR to the HFR, wherein the one or more fluid conduits transfer undigested biomass from the ADR to the HFR and hydrolysis products from the HFR to the ADR.

In one aspect, the ADR is maintained at mesophilic or thermophilic temperatures and the HFR is maintained at thermophilic temperatures. In one aspect, the HFR contents undergo recuperative thickening to increase solids retention time in the HFR.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments and implementations and illustrated in the accompanying drawings.

DETAILED DESCRIPTION

Figure 1:
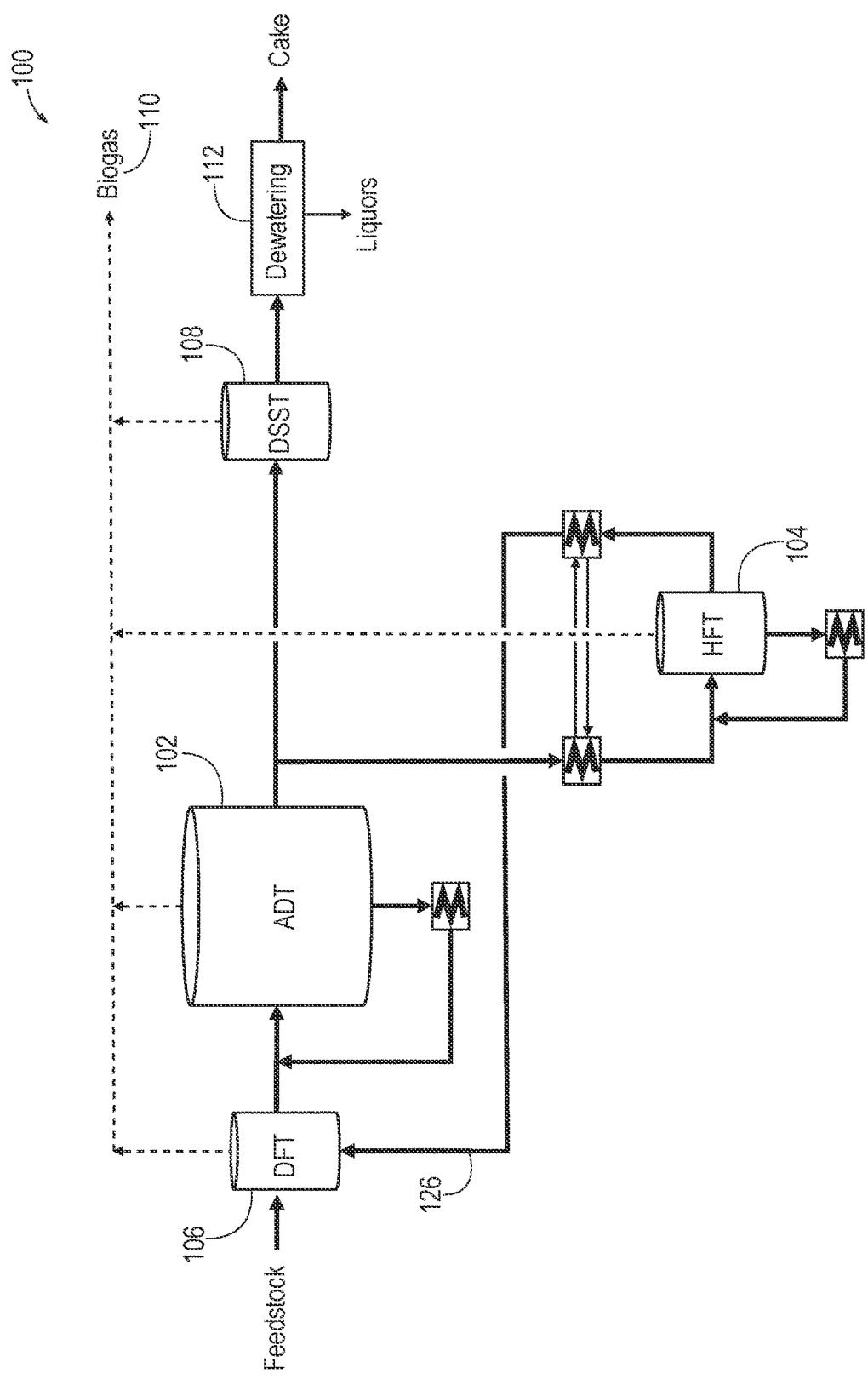
FIG. 1 is a diagram depicting a system for improving anaerobic digestion with a post-anaerobic digestion process.

This disclosure is related to systems and methods for improving performance of anaerobic digestion by post-anaerobic digestion processing. The systems and methods disclosed herein include using microorganisms in a post-anaerobic digestion process to further process one or more products of anaerobic digestion. In several embodiments, the microorganisms used in the post-anaerobic digestion process are anaerobic microbes that hydrolyze and ferment anaerobic digestion products. Anaerobic digestion products include biosolids (also known as digestate), which include products refractory to digestion, and biogas. In several embodiments, the post-anaerobic digestion microorganisms hydrolyze and ferment the biosolids or digestate to increase organic conversion and biogas production from the anaerobic digestion process.

The systems and methods of the present disclosure may include an anaerobic digestion (AD) process and a post-anaerobic digestion (post-AD) process. During the AD process, microorganisms, referred to herein as anaerobic digestion (AD) microorganisms, receive feedstock and digest the feedstock to produce biosolids and biogas. During the post-AD process, microorganisms, referred to herein as post-AD or hydrolysis and/or fermentation (H/F) microorganisms, receive the biosolids produced during the AD process and hydrolyze and/or ferment the biosolids to produce hydrolysis and/or fermentation (H/F) products, including, for example, fatty acids, sugars, amino acids, smaller VFAs, alcohols, acetic acid, lactate acid, hydrogen gas, carbon dioxide, and the like. These H/F products are fed to an AD process to produce additional biogas. While the post-AD process may be described herein as a hydrolysis and fermentation process and the post-AD process products may be described herein as hydrolysis and fermentation products, it is contemplated that one or both of these processes and respective products may be part of the post-AD process (i.e., one or both of hydrolysis and fermentation may occur during the post-AD process, producing one or both of hydrolysis and fermentation products, respectively). Some embodiments may include an additional AD process to further digest one or more of the H/F products produced from the post-AD process to generate additional biogas. As discussed in more detail below, some embodiments may further include a pre-digestion or pre-anaerobic digestion (pre-AD) treatment to further improve solids digestion during the AD process.

A post-AD process of the present disclosure may be added to any anaerobic digestion system. The post-AD process is compatible with and does not compete with other hydrolysis processes. In other words, the post-AD process can focus on hydrolysis of the biosolids or digestate, without the distraction of hydrolysis of other food sources. This non-competitive post-AD process provides greater efficiency in biogas production than current processes that are limited by competing hydrolysis processes (e.g., certain pretreatment processes). This enhanced anaerobic digestive performance further reduces the amount of residual biosolids that require increased costs for handling or disposal. In this manner, the disclosed post-AD process increases the efficiency and reduces the costs of anaerobic digestion systems.

Microorganisms

Microorganisms used with the disclosed systems and methods may include one or more anaerobic microbes. The disclosed anaerobic microbes are capable of anaerobic digestion of feedstock and/or hydrolysis and/or fermentation of digestate, plastics, and other pollutants. Microbes of the present disclosure may include bacteria, archaea, protozoa, or the like. The disclosed microorganisms may include, for example, thermophilic microbes, mesophilic microbes, cellulolytic microbes, hemicellulolytic microbes, glycolytic enzymes microbes, methanogens (e.g., acetoclastic, hydrogenotrophic, etc.), and the like. Thermophilic microbes (i.e., thermophiles) thrive at relatively high temperatures, for example between 41° C. and 122° C. Mesophilic microbes (i.e., mesophiles) thrive at moderate temperatures, for example between 20° C. and 45° C. Cellulolytic microbes degrade cellulose and produce cellulases, and may include bacteria selected from the genus *Trichonympha, Mixotricha, Ruminococcus*, and/or *Clostridium*, etc. Hemicellulolytic microbes ferment various types of hemicelluloses, and may include bacteria selected from the genus *Butyrivibrio, Clostridium*, and/or *Bacteroides*. Glycolytic enzymes microbes have glycolytic enzymes that convert cellulose into malate, which can be further fermented to carbon dioxide, hydrogen, and acetate. Methanogens are organisms that produce methane. For example, acetoclastic methanogens convert acetate into methane and carbon dioxide, while hydrogenotrophic methanogens use hydrogen for the reduction of carbon dioxide to methane and water.

As another example, the disclosed microbes may include one or more microbes selected from genus *Caldicellulosiruptor, Clostridium, Thermoanaerobacterium, Bacillus, Ochroabactrum*, and/or *Microbacterium*. For example, the disclosed anaerobic microbes may include *Caldicellulosiruptor bescii (C. bescii), Clostridium thermocellum (C. thermocellum), Thermoanaerobacterium saccharolyticum (T. saccharolyticum), Bacillus licheniformis (B. licheniformis), Ochroabactrum intermedium (O. intermedium)*, and/or *Microbacterium paludicola (M. paludicola)*.

*Caldicellulosiruptor bescii*, previously known as "*Anaerocellum thermophilum*" and now referred to as *C. bescii*, is an anaerobic bacterium that was originally isolated from the hot springs in the valley of Geysers, Kamchatka, Russia (Svetlichnyl 1990). This microorganism grows on cellulose with an optimal temperature of around 78° C. at pH 7 and is among the most thermophilic celluloytic organisms discovered to date (Yang 2009). It is showing promise to ferment recalcitrant materials such as crystalline cellulose, hemicellulosic sugars, and plant biomass such as hardwood poplar, switchgrass (*Panicum virgatum*) and elephant grass (*Pennisetum purpureum*), producing acetate, lactate, and hydrogen (Blumer-Schuette 2008). Previous research has focused on ethanol production from lignocellulosic biomass using engineered *C. bescii* strains under batch conditions (Chung 2015).

Anaerobic Digestion Process

Disclosed systems and methods may include an anaerobic digestion process. During the AD process, microorganisms, also known as AD microorganisms, receive feedstock and digest the feedstock to produce biosolids and biogas.

Feedstock used for the AD process may include various types of organic material. For example, feedstock may include primary sludge, waste activated sludge (WAS), fats, oils and grease (FOG), food waste, organic fraction of municipal solid waste (OFMSW), cow manure, and the like. Some organic material digests better than others and is measured as the percent of volatile solids reduced (VSR). For example, primary sludge has a VSR of 50-70 percent, waste activated sludge (WAS) has a VSR of 20-40 percent, and fats, oils, and grease (FOG) has a VSR of over 90 percent.

The AD microorganisms may include one or more of the microorganisms discussed above. For example, the AD microorganisms may include one or more of thermophilic microbes, mesophilic microbes, cellulolytic microbes, hemicellulolytic microbes, glycolytic enzymes microbes, methanogens, and the like.

The products of the AD process include biosolids, also known as digestate, and biogas. Biogas is composed of methane, carbon dioxide, water vapor, hydrogen sulfide, and small amounts of other compounds. The digestate includes residual biosolids that are refractory to digestion and include recalcitrant materials. For example, waste activated sludge is a recalcitrant organic material because of its microbial cell membranes. As another example, the portion of primary sludge that is refractory to digestion contains toilet paper or lignocellulosic material. In conventional anaerobic digestion processes, the residual recalcitrant solids in the digestate may need further processing and handling for beneficial use or disposal; however, the present disclosed systems and methods make use of this recalcitrant solids with a post-anaerobic digestion process to enable their conversion into biogas.

Post-Anaerobic Digestion Process

Disclosed systems and methods include a post-anaerobic digestion process. The post-AD process may be an efficient hydrolysis and fermentation process that hydrolyzes and ferments the digestate produced during the AD process to produce H/F products. For example, the post-AD process may include microorganisms, also known as post-AD microorganisms, that hydrolyze and/or ferment recalcitrant material (e.g., lignocellulosic biomass) in the digestate. The post-AD process may be considered a solids contact process that hydrolyzes and ferments biosolids using anaerobic microbes.

The food supplied to the post-AD process is digestate produced by anaerobic digestion. The digestate includes indigestible material. For example, the digestate includes recalcitrant materials, which are generally resistant to microbial decomposition. As one example, the digestate includes recalcitrant lignocellulosic biomass. The recalcitrant materials remain in the digestate even in instances where a pretreatment process was implemented prior to the anaerobic digestion process.

Post-AD microorganisms are capable of digesting the recalcitrant biomass in the digestate. For example, post-AD microorganisms used for a post-AD process of the present disclosure may include one or more of the microorganisms discussed above. For example, the post-AD microorganisms may include one or more of thermophilic microbes, mesophilic microbes, cellulolytic microbes, hemicellulolytic microbes, glycolytic enzymes microbes, methanogens, and the like. As one example, the post-AD microorganisms may be thermophilic celluloytic organisms. The post-AD microorganisms may include one or more microbes selected from genus *Caldicellulosiruptor, Clostridium, Thermoanaerobacterium, Bacillus, Ochroabactrum, Microbacterium, Trichonympha,* and/or *Mixotricha*. For example, the post-AD microorganisms may include *Caldicellulosiruptor bescii* (*C. bescii*), *Clostridium thermocellum* (*C. thermocellum*), *Thermoanaerobacterium saccharolyticum* (*T. saccharolyticum*), *Bacillus licheniformis* (*B. licheniformis*), *Ochroabactrum intermedium* (*O. intermedium*), and/or *Microbacterium paludicola* (*M. paludicola*).

As one example, the post-AD microorganisms may include *C. bescii* microbes. The *C. bescii* microbes may be primarily fed the undigested products from the AD process (e.g., the recalcitrant material (solids) that the AD process is unable to digest). In other words, the undigested AD products may not compete with other food sources for digestion by the *C. bescii* microbes. Further, the digestate has ample alkalinity to maintain a neutral pH and has a low concentration of sugars (because sugars are readily digestible and have already been digested), so the *C. bescii* are not distracted. Without distraction by other food sources, the *C. bescii* microbes can more efficiently digest the undigested AD products.

As another example, *C. thermocellum* may be used to hydrolyze the recalcitrant biomass. *C. thermocellum* has the ability to convert cellulosic biomass into ethanol, acetate, lactate, formate, carbon dioxide, hydrogen, and amino acids (Chung 2013). *C. thermocellum* grows at an optimal temperature of around 60° C. As another example, *T. saccharolyticum* may be used in the post-AD process. *T. saccharolyticum* is a thermophilic, anaerobic, hemicelluloytic bacterium that is able to ferment hemicellulose, xylan polymers, and sugars in cellulosic biomass. Sugars include cellobiose, glucose, zylose, mannose, galactose, and arabinose. *T. saccharolyticum* grows at pH values ranging from 3.85 to 6.35 and at temperatures ranging from 30° C. to 55° C. (Shaw 2008). As yet another example, cellulolytic protists (e.g., from genus *Trichonympha* and/or *Mixotricha*), which produce cellulases, may be used in the post-AD process. As another example, various glycolytic enzymes protozoa may be used in the post-AD process that convert cellulose into malate that can be further fermented to carbon dioxide, hydrogen, and acetate. (Ohkuma 2006). As yet another example, one or more of bacterial strains *B. licheniformis, O. intermedium,* and *M. paludicola* may be used in the post-AD process. *B. licheniformis, O. intermedium,* and *M. paludicola* have optimum growth at a pH of 7.0 with temperatures of 37° C. to 40° C.

The post-AD microorganisms hydrolyze and ferment the digestate to produce hydrolysis and fermentation products. The hydrolysis and fermentation products may be in the form of, for example, fatty acids, sugars, amino acids, smaller VFAs, alcohols, acetic acid, lactate acid, hydrogen gas, and carbon dioxide.

The hydrolyzed and fermented products produced from the post-AD microorganisms may be fed to AD microorganisms to be converted to biogas (methane and carbon dioxide) through methanogenesis to complete the anaerobic digestion process.

Pre-Anaerobic Digestion Treatment

Systems and methods of the present disclosure may include one or more pre-anaerobic digestion treatments. Pre-anaerobic digestion treatments, also known as pre-digestion or pretreatment processes, process the feedstock or organic material before it is fed to the AD microorganisms to make the feedstock or organic material easier for digestion by the AD microorganisms. For example, a pre-digestion process may break down the feedstock or organic material to improve the solids conversion, produce more biogas, reduce the amount of residual biosolids, and improve dewatering during the AD process. Pre-digestion (pretreatment) processes may include conventional pretreatment processes, such as, for example, biological hydrolysis (e.g., acid phase, enzymatic hydrolysis, etc.), mechanical hydrolysis, acid hydrolysis, thermal hydrolysis, thermal/chemical hydrolysis, and pretreatment C. bescii hydrolysis.

As one example, biological hydrolysis includes pretreatment processes such as acid phase and enzymatic hydrolysis. As another example, thermal hydrolysis is a pretreatment process to improve the solids conversion, produce more biogas, reduce the amount of residual biosolids, and improve dewatering. However, most lignocellulosic and other recalcitrant materials are not hydrolyzed by the thermal hydrolysis process nor other pretreatment processes and remain in the digestate. In some examples, post-AD microorganisms in accordance with the disclosed systems and methods, are capable of digesting the recalcitrant biomass in the digestate and can be used in combination with a pretreatment step.

Systems for Improving Anaerobic Digestion

Systems of the present disclosure improve the efficiency and performance of anaerobic digestion. For example, disclosed systems increase the rate of anaerobic digestion, reduce recalcitrant biomass, and increase biogas production. Disclosed systems may include a feed or recycle loop, which transfers digestive products between anaerobic and post-AD microorganisms for further digestion. For example, anaerobic digestive products may include digestate that is transferred from AD microorganisms to post-AD microorganisms for hydrolysis and fermentation. As another example, post-anaerobic digestive products may include H/F products that flow from the post-AD microorganisms to AD microorganisms for anaerobic digestion.

FIG. 1 shows an exemplary system 100 having an anaerobic digestion receptacle or reactor (ADR), also known as an anaerobic digestion tank (ADT) 102, and a post-anaerobic digestion receptacle or reactor, also known as a hydrolysis/fermentation receptacle or reactor (HFR) or a hydrolysis/fermentation tank (HFT) 104. A receptacle described herein may be a container, housing, vessel, vat, repository, tank, reactor, or the like. The ADR 102 may store AD microorganisms in an environment having conditions selected for improved growth of the AD microorganisms. For example, the controlled environmental conditions may include temperature, pH, nutrients, acids, alkalinity, ammonia, and the like. As one example, the temperature may be thermophilic or mesophilic. A thermophilic temperature may be a relatively high temperature, for example, between 40° C. and 80° C., between 40° C. and 50° C., between 50° C. and 60° C., between 60° C. and 70° C., between 70° C. and 80° C., and the like. A mesophilic temperature may be a moderate temperature, for example, between 25° C. and 40° C., between 30° C. and 35° C., between 40° C. and 45° C., and the like. As one example, the ADR 102 is maintained at about 35° C., about 36° C., about 37° C., about 38° C., about 39° C., about 40° C., about 50° C., about 51° C., about 52° C., about 53° C., about 54° C., about 55° C., about 56° C., about 57° C., about 58° C., about 59° C., or about 60° C. As another example, the pH may be acidic, neutral or close to neutral, or basic. For example, the pH may be 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5 or the like.

The capacity of the ADR 102 and/or the biomass concentration of AD microorganisms may be varied to accommodate different feed rates. For example, increasing the biomass concentration and consequently the microorganism population of the ADR 102 increases the capacity to accept greater feed rates. The biomass concentration may be measured in terms of volatile solids concentration in the ADR 102, for example, with a range of around 1 to 6 percent, or about 0.5%, 1%, 1.5%, 2%, 2.5%, 3%, 3.5%, 4% 4.5%, 5%, 5.5%, 6% or 6.5%.

The HFR 104 may store post-AD microorganisms in an environment having conditions selected for improved growth of the post-AD microorganisms. For example, the controlled environmental conditions may include temperature, pH, nutrients, acids (e.g., acetate), alkalinity, ammonia, and the like. As one example, the temperature may be thermophilic or mesophilic. A thermophilic temperature may be a relatively high temperature, for example, between 40° C. and 80° C., between 40° C. and 50° C., between 50° C. and 60° C., between 60° C. and 70° C., between 70° C. and 80° C., and the like. A mesophilic temperature may be a moderate temperature, for example, between 25° C. and 40° C., between 30° C. and 35° C., and the like. As one example, the HFR 104 is maintained at about 75° C., about 76° C., about 77° C., about 78° C., about 79° C., about 80° C. As another example, the pH may be neutral or close to neutral. For example, the pH may be 6.5, 6.6, 6.7, 6.8, 6.9, 7.0, 7.1, 7.2, 7.3, 7.4, 7.5, or the like.

As discussed above, the post-AD microorganisms may include C. bescii. In this example, the HFR 104 environment may have conditions optimal for C. bescii. For example, the HFR 104 environment may include cellulose and other recalcitrant compounds (e.g., undigested waste activated sludge). The HFR 104 environment may have an optimal temperature of about 74° C., about 75° C., about 76° C., about 77° C., about 78° C., about 79° C., or about 80° C., and a pH of about 6.8, about 6.9, about 7.0, about 7.1, or about 7.2. As another example, the post-AD microorganisms may include B. licheniformis, O. intermedium, and/or M. paludicola. In this example, the HFR 104 environment may have conditions optimal for B. licheniformis, O. intermedium, and/or M. paludicola. For example, the HFR 104 environment may have an optimal temperature of about 37° C. to about 40° C. and a pH of about 7.0.

The capacity of the HFR 104 and/or the biomass concentration of the HRF may be varied to accommodate different feed rates. For example, increasing the biomass concentration and consequently the microorganism population of the HFR 104 increases the capacity to accept greater feed rates. As one example, the biomass concentration may be measured in terms of volatile solids concentration in the HFR 104, for example, with a range of around 1 to 6 percent, or about 0.5%, 1%, 1.5%, 2%, 2.5%, 3%, 3.5%, 4% 4.5%, 5%, 5.5%, 6% or 6.5%; however, other conventional methods of measuring biomass concentration are contemplated.

As shown in FIG. 1, the ADR 102 and HFR 104 may be coupled by one or more fluid conduits 126. For example, a fluid conduit 126 may be or include a pipe, tube, channel, tubular body, or the like. The one or more fluid conduits 126 may provide a channel for the digestion products to move from the ADR 102 to the HFR 104, from the HFR 104 to the ADR 102, or in both directions. For example, a fluid conduit 126 may pass (e.g. transmit, transfer, distribute, or allow to flow) digestate from the ADR 102 to the HFR 104. As another example, a fluid conduit 126 may pass H/F products from the HFR 104 to the ADR 102. As yet another example, a fluid conduit 126 may pass digestate from the ADR 102 to the HFR 104 and H/F products from the HFR 104 to the ADR 102. In this example, the fluid conduit 126 may include a pump and valve. For example, if the digestion product originates in the ADR 102 (e.g., digestate), the flow direction (direction of flow) is from the ADR 102 to the HFR 104. If the digestion product originates in the HFR 104 (e.g., H/F products), the flow direction is from the HFR 104 to the ADR 102. In some embodiments, the one or more fluid conduits 126 may include one or more pumps that pump the fluids (e.g., digestion products) between different receptacles.

The system 100 may include additional receptacles for storage (e.g., of biogas, byproducts, waste products, etc.) and/or additional processing. These additional receptacles may be coupled to one or more ADRs, to one or more HFRs, and/or to each other, by one or more of the fluid conduits 126 discussed above. While only one ADR 102 and HFR 104 is shown in the figures, multiple ADRs and HFRs are contemplated. As shown in FIG. 1, for example, the system 100 may include one or more of a digester feed receptacle (DFR), also known as a digester feed tank (DFT) 106, a digestate storage receptacle (DSR), also referred to as a digested sludge storage tank (DSST) 108, a biogas storage receptacle (BSR), and a biogas sub-system 110, in any combination thereof. As one example, a digester feed receptacle (DFR) 106 may store feedstock before it is introduced to one or more ADRs. As shown, the DFR 106 may receive and store H/F products from one or more HFRs. The DFR 106 may transfer feedstock and/or H/F products to one or more ADRs. As another example, a digestate storage receptacle (DSR) 108 may store digestate (e.g., digested sludge) (e.g., produced in one or more ADRs) before the digestate is dewatered in a dewatering receptacle 112. As shown, the DSR 108 may receive and store digestate from one or more ADRs. Digested sludge (digestate) includes mostly liquid with lesser amounts of digested solid material. The digestate may be transferred from the DSR 108 to the dewatering receptacle 112 to undergo a dewatering process. For example, the dewatering receptacle 112 may include solids separation equipment that separates the liquids and solids in the digestate, producing a relatively dry cake from the separated solids and a liquor from the separated liquids. Conventional dewatering equipment such as, for example, a high solids centrifuge, screw press, belt filter press, and the like may be used. This dewatering process may facilitate transport for beneficial use or disposal of the digestate.

In some embodiments, a biogas storage receptacle (BSR) may be included with the disclosed system 100 and may provide a location to store biogas; however, it is also contemplated that a system of the present disclosure may exclude the BSR and instead transfer biogas produced by the system 100 to a biogas sub-system 110 for beneficial use, e.g., as shown in FIG. 1. In some embodiments, one or more of the receptacles (e.g., ADR 102, HFR 104, DFR 106, DSR 108) may include a gas space for receiving biogas produced within the receptacle. If a BSR is included with the system 100, such receptacles may be coupled to the BSR and biogas flows from the respective receptacle to the BSR. In instances in which no BSR is included, the receptacles may be coupled to a biogas sub-system 110 and biogas flows from the respective receptacle to the biogas sub-system 110. As one example, biogas produced by anaerobic digestion in the ADR 102 may flow from the ADR 102 through a fluid conduit 126 to the BSR or the biogas sub-system 110. The biogas may be treated to remove hydrogen sulfide, siloxanes, and the like, and used to fuel combined heat and power (CHP) units to produce electricity and heat, or further treated to remove carbon dioxide and used as a renewable natural gas fuel, and the like.

Figure 5:
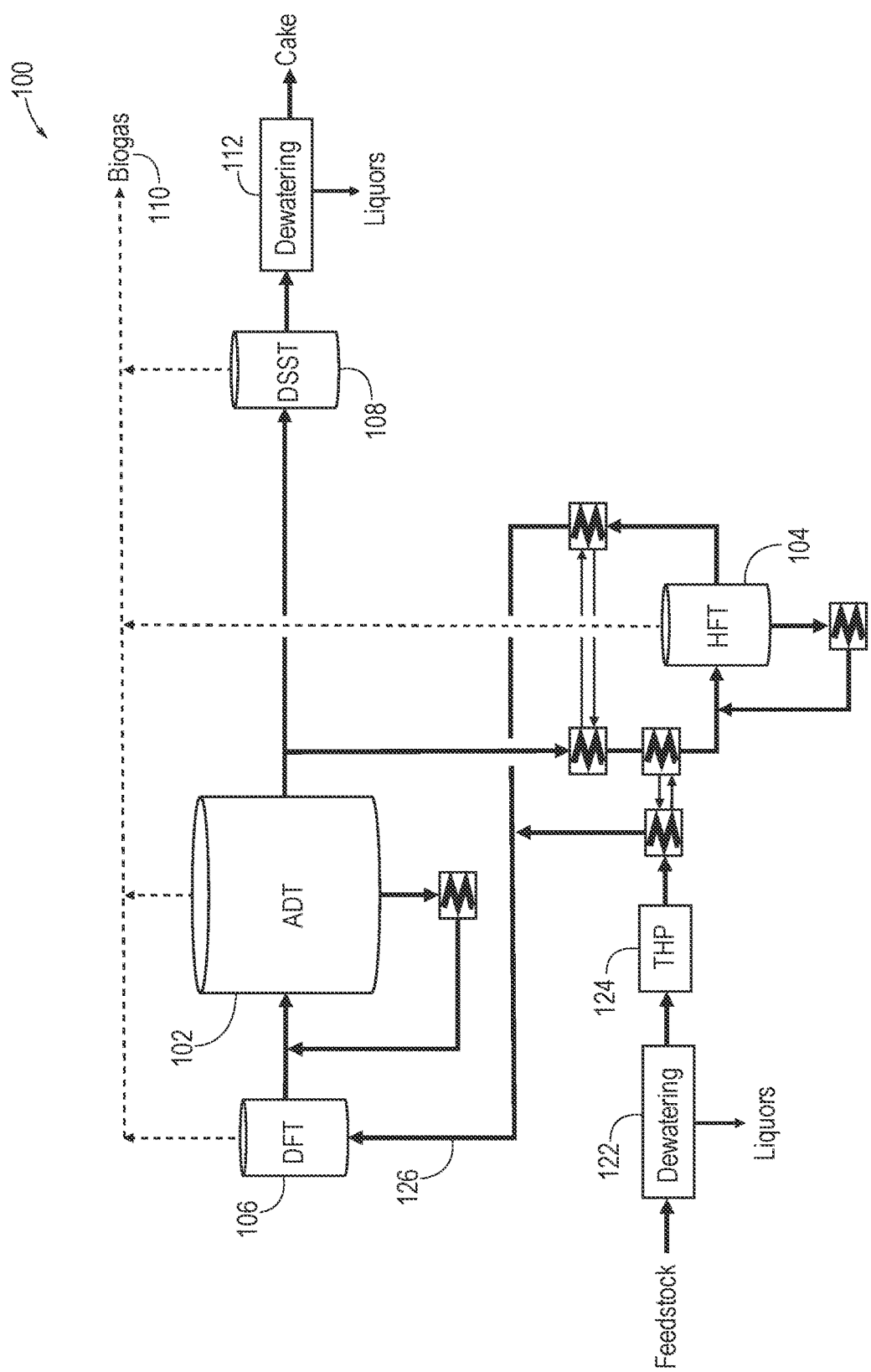
FIG. 5 is a diagram depicting another system for improving anaerobic digestion with a post-anaerobic digestion process that includes a pre-anaerobic digestion thermal hydrolysis process.

In some embodiments, the system 100 may include one or more pretreatment receptacles. For example, as shown in FIG. 5, the system 100 may include a pre-digestion dewatering receptacle 122 and a thermal hydrolysis receptacle 124. As shown, the pre-digestion dewatering receptacle 122 may receive feedstock and process the feedstock to remove liquors. The processed feedstock may pass from the pre-digestion dewatering receptacle 122 to the thermal hydrolysis receptacle 124 to undergo a thermal hydrolysis process before being transferred to the DFR 106 and then to the ADR 102, or directly to the ADR 102.

In an exemplary implementation of a system described herein, feedstock may be introduced to the ADR 102 to feed the AD microorganisms. As shown in FIG. 1, feedstock may be introduced to the DFR 106 where it is stored before being introduced to the ADR 102. In some embodiments, the feedstock may go through one or more of the disclosed pretreatment processes (e.g., thermal hydrolysis as shown in FIG. 5) discussed above before being introduced to the DFR 106 and/or ADR 102. The anaerobic digestion process discussed above occurs in the ADR 102. As discussed, the AD microorganisms in the ADR 102 digest the feedstock to produce biogas and biosolids or digestate. As shown in FIG. 1, the biogas is collected from the ADR 102 and sent to a biogas sub-system 110. A biogas conduit 126 is shown connected to the DFR, ADR, HFR, and DSR 108. Digestate or biomass flows or is pumped from the ADR 102 to the DSR 108 before being dewatered with the dewatering receptacle 112 (e.g., solids separation equipment) and beneficially used or disposed.

Biomass that was not digested in the ADR 102 (e.g., cellulosic and recalcitrant biomass) and is contained in the digestate flows or is pumped from the ADR 102 to the HFR 104 to feed the post-AD microorganisms stored in the HFR 104. For example, the digestate may be the primary food for the post-AD microorganisms (e.g., *C. bescii*). The digestate provides micro-nutrients and a natural alkalinity to maintain a neutral pH around 7.0, providing an environment that is optimal for growth of various described post-AD microorganisms in the HFR. The post-anaerobic digestion process discussed above occurs in the HFR 104. As discussed, the post-AD microorganisms in the HFR 104 hydrolyze and ferment the digestate to produce hydrolysis and fermentation products.

The retention time in the HFR 104 may be selected based on the rate of hydrolysis and/or fermentation of the cellulosic and recalcitrant biomass. In other words, retention time may correspond to the amount of time required for the biomass to hydrolyze and/or ferment. For example, the required retention time for hydrolysis and/or fermentation may vary based on the concentration of post-AD microorganisms in the HFR 104 and their reaction rate (e.g., the retention time may be inversely proportional to the concentration and reaction rate). As one example, retention time of the recalcitrant biomass may be increased by recuperative thickening. Recuperative thickening may include a solids separation step, return of the solids to the HFR 104 for further processing, and transfer of the liquor containing the hydrolysis and fermentation products to the ADR 102. As one example, retention time in the HFR 104 may be about 1 day to about 6 days, about 2 days to about 5 days, about 3 days to about 4 days, and the like. Without recuperative thickening, the hydraulic and solids retention time may be equal and are controlled by the controlling the amount of digestate fed to the HFR 104 and the volume of the HFR 104. With recuperative thickening, the solids retention time is increased by returning solids to the HFR 104. The hydraulic retention time, on the other hand, is not increased with recuperative thickening.

As shown in FIG. 1, the hydrolysis and fermentation products flow from the HFR 104 to the ADR 102 for additional anaerobic digestion. The additional anaerobic digestion may produce additional biogas, digested sludge, and/or digestate. Additional biogas is collected from the ADR 102 and used in a biogas sub-system 110. Additional digestate or biomass flows or is pumped from the ADR 102 to the DSR 108 before being dewatered and beneficially used (e.g., as a soil amendment or other use) or disposed. Additional digestate flows to the HFR 104 for additional post-AD processing as described above.

Heat may be exchanged between the various receptacles, e.g., between the ADR 102 and HFR 104, to conserve energy. For example, the digestate flowing from the ADR 102 may pass through heat exchangers to increase its temperature closer to the HFR 104 temperature, while hydrolyzed and fermented digestate flowing from the HFR 104 may pass through heat exchangers to decrease its temperature closer to the ADR 102 temperature. In this example, heat exchangers may provide for heat recovery from the HFR 104 fluid flowing to the ADR 102 and provide heat to the fluid flowing to the HFR 104. Heat exchangers may also provide additional heating to maintain HFR temperature and cooling to maintain ADR 102 temperatures. The circulation rate between the receptacles (e.g., the ADR 102 and HFR 104) may be controlled and may correspond to the size of the ADR 102, the post-AD microorganism population (e.g., C. bescii microbial population) in the HFR 104, and/or the retention time in the ADR 102 and/or HFR 104. As one example, the circulation rate may be controlled by pumps.

Figure 2:
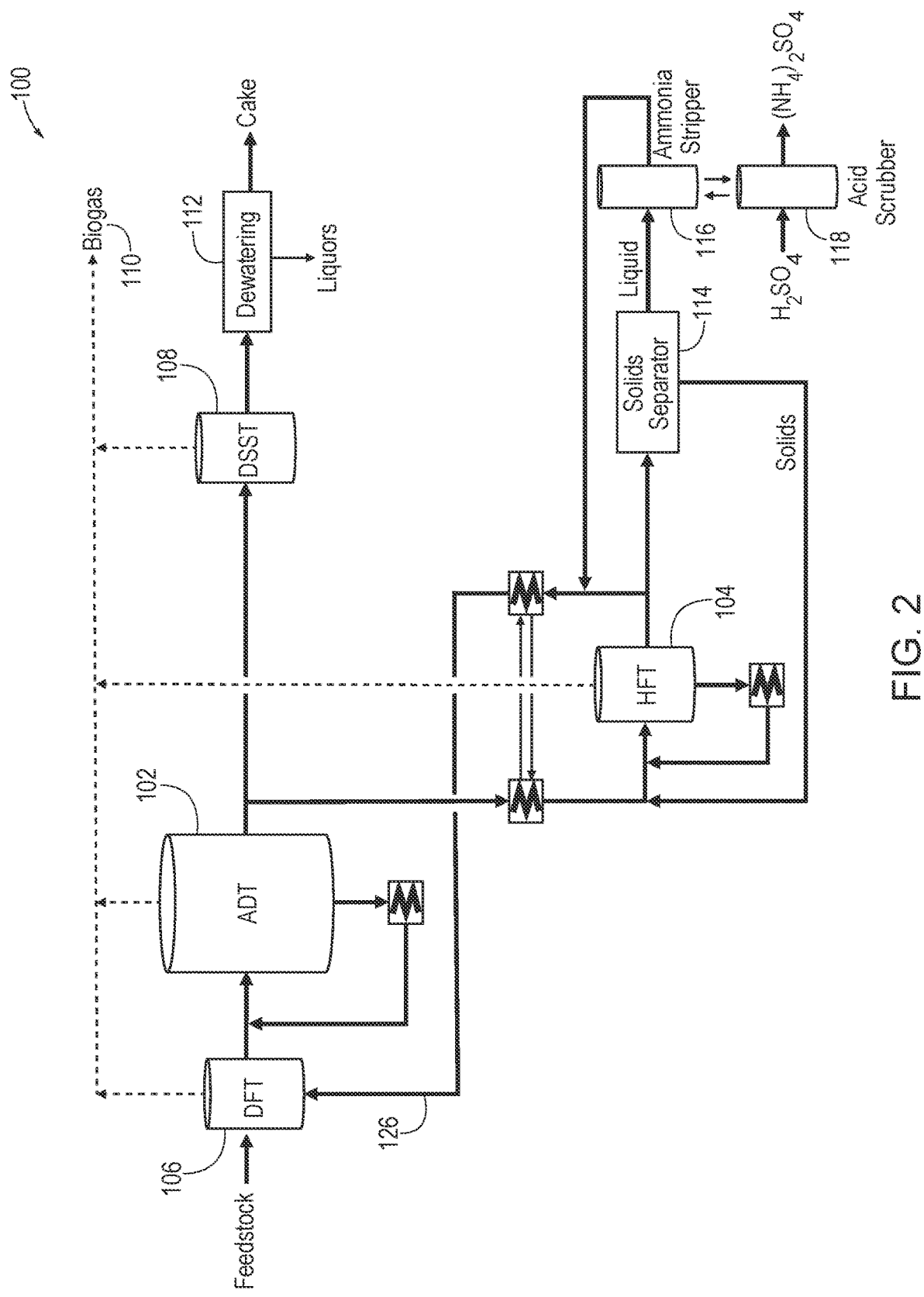
FIG. 2 is a diagram depicting another system for improving anaerobic digestion with a post-anaerobic digestion process that includes additional downstream processing.
Figure 3:
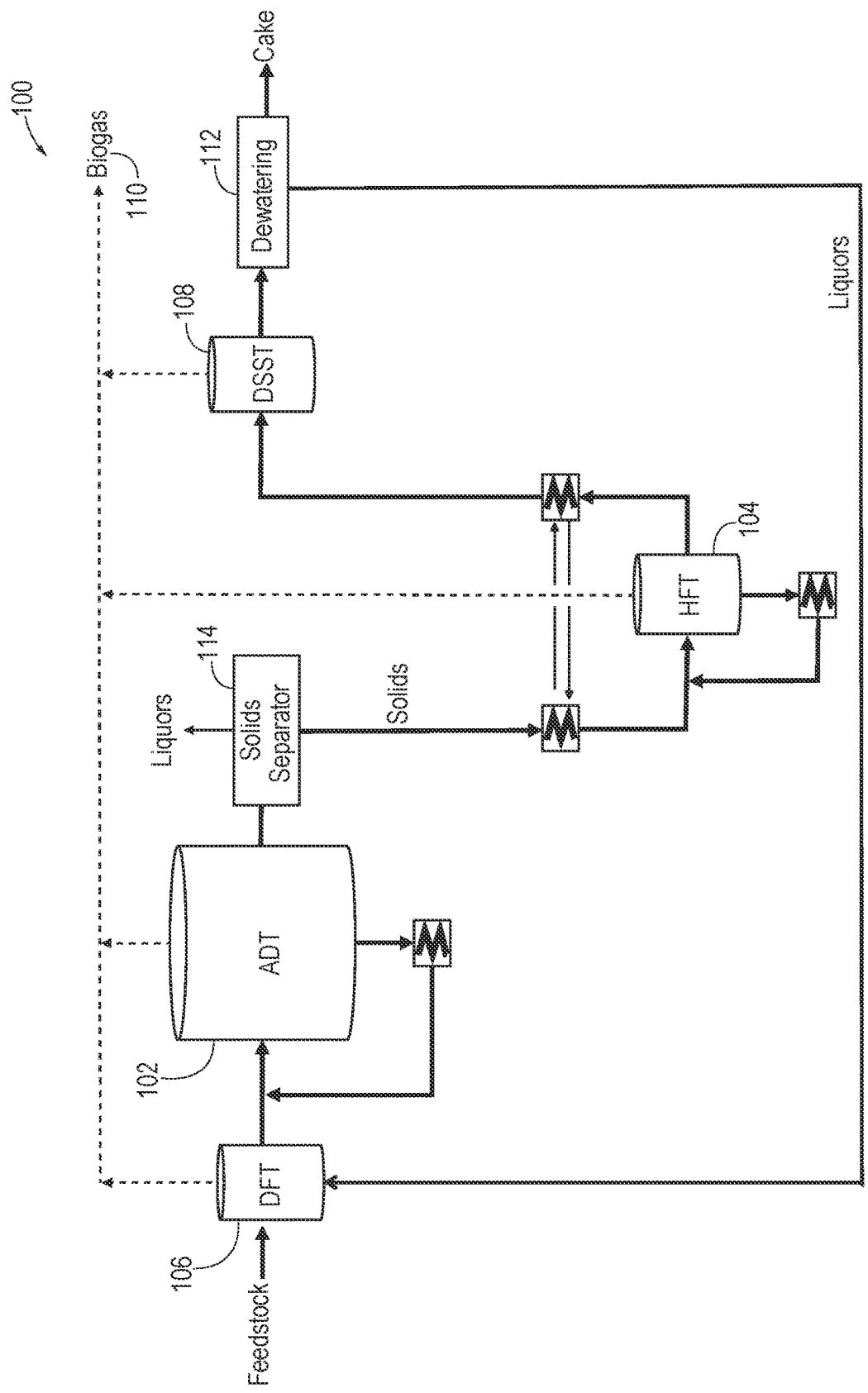
FIG. 3 is a diagram depicting another system for improving anaerobic digestion with a post-anaerobic digestion process that includes a downstream dewatering process.

In some embodiments, the system 100 may include additional receptacles or reactors or processes for additional processing of the digested products. For example, the system 100 may include one or more of a solids separator receptacle 114, an ammonia removal receptacle (e.g., ammonia stripper 116 and acid scrubber 118), and a digestate dewatering receptacle 112. One or more of the processes may be combined and or not utilized at all. For example, as shown in FIG. 2, a solids separator receptacle 114 may be coupled to the HFR 104 and may receive the H/F products before they are transferred to the ADR 102. In this example, the solids separator receptacle 114 separates solids and liquids in the H/F products. As shown, the solids may be transferred back to the HFR 104 for further hydrolysis and fermentation. As another example, as shown in FIG. 3, a solids separator receptacle 114 may be coupled to the ADR 102 and may receive the digestate before it is transferred to the HFR 104. In this example, the solids separator receptacle 114 separates solids and liquids in the digestate. As shown, the liquids, or liquors, may be collected from the solids separator receptacle 114, and the solids may be transferred to the HFR 104 for hydrolysis and fermentation. It is contemplated that a solids separator receptacle 114 may be used anywhere throughout the system 100, coupled to any of the various receptacles described herein as applicable. The solids separator 114 may reduce liquid buildup in the system 100.

As shown, the solids separator receptacle 114 may be coupled to an ammonia stripper or ammonia removal receptacle 116 and may transfer liquids to the ammonia removal receptacle 116. The ammonia removal receptacle 116 may remove ammonia from the liquid H/F product. The ammonia removal receptacle 116 may include conventional means for removing ammonia. For example, the ammonia removal receptacle may increase the pH and temperature of the liquid to remove ammonia. As one example, if the post-AD microorganism is thermophilic bacteria (e.g., C. bescii), the liquid will already be at an ammonia stripping temperature (e.g., about 75° C.), and a base or alkali (e.g., sodium hydroxide) may be added to control the pH in the ammonia removal receptacle.

In some embodiments, for example as shown in FIG. 2, the ammonia removal receptacle 116 may be coupled to an acid scrubber receptacle 118 and liquids may pass or flow therebetween. The acid scrubber receptacle 118 may house an acid, such as, for example, sulfuric acid. The ammonia stripped by the ammonia removal receptacle 116 reacts with the acid to produce ammonium ions. As one example, the acid scrubber receptacle 118 includes sulfuric acid, which reacts with the ammonia to produce ammonium sulfate. The ammonium sulfate may be collected and used, for example, as a fertilizer.

As shown, the H/F product liquid from the HFR 104 may be returned to the ADR 102 having a lower ammonia concentration after flowing through the ammonia removal receptacle. The digestate produced from anaerobic digestion of the lower ammonia-containing H/F products may also have reduced ammonia concentration. This reduced ammonia digestate may be fed to the HFR 104. The reduced ammonia digestate may be important in some embodiments where ammonia at high concentrations is toxic to the post-AD microorganisms housed in the HFR 104, such as, for example, C. bescii.

In some embodiments, the system 100 may include a dewatering receptacle 112. For example, instead of the effluent flowing from the HFR 104 directly to the ADR 102, as shown in FIG. 1, the effluent returned to the ADR 102 may first be transferred from the HFR 104 to a DSR 108 for dewatering in a dewatering receptacle 112, as shown in FIG. 3. The dewatering (solids separator) receptacle 112 removes liquid H/F products from the HFR 104 products. In this example, only the liquid H/F products are returned to the DFR 106 and fed to the ADR 102 or returned directly to the ADR 102. The solid products (e.g., digested solids) may be distributed and beneficially used or may undergo further processing (e.g., may be returned to the HFR 104 for additional hydrolysis and fermentation).

Figure 4:
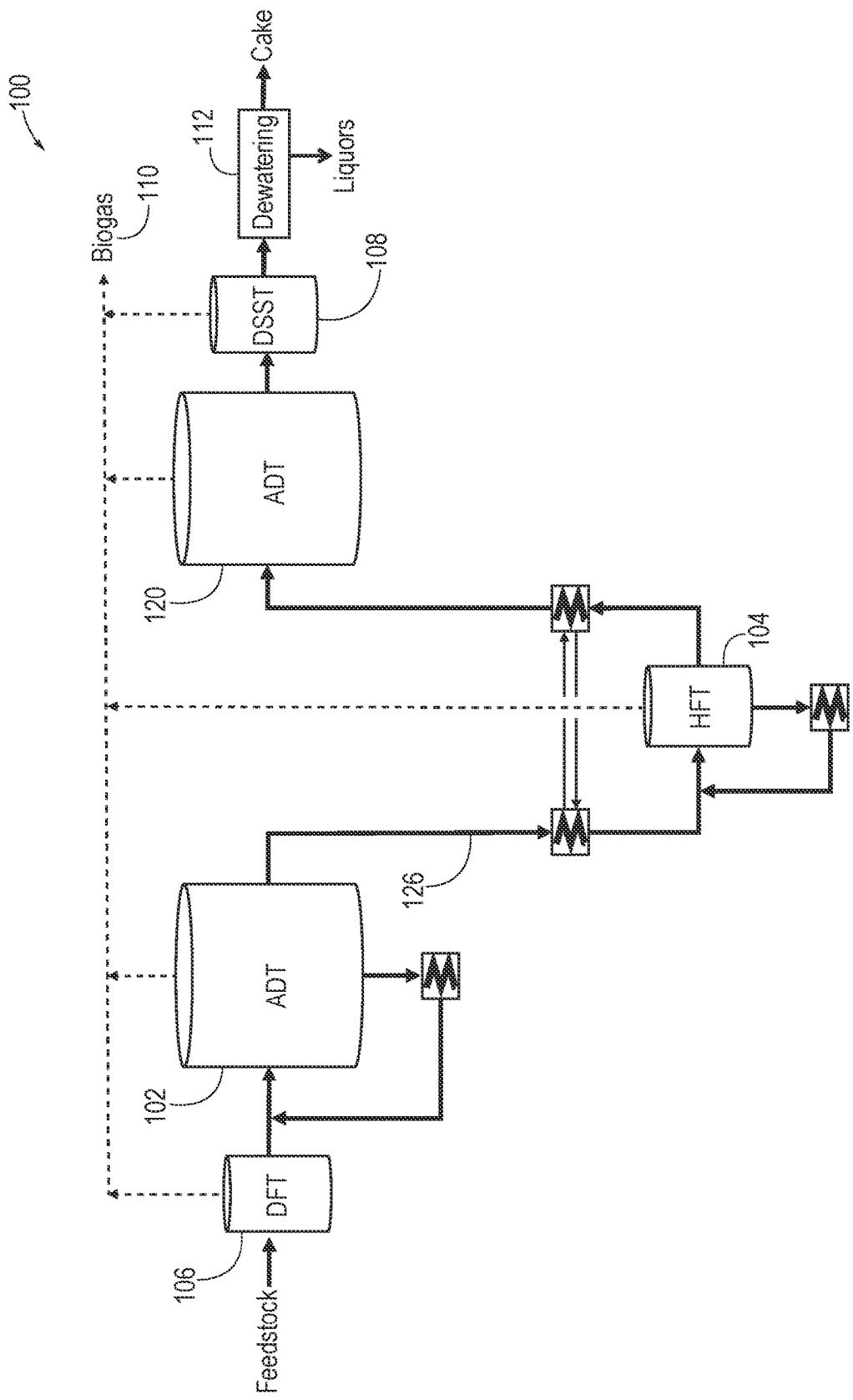
FIG. 4 is a diagram depicting another system for improving anaerobic digestion with a post-anaerobic digestion process that includes two separate anaerobic digestion processes.

In some embodiments, the system 100 may include multiple ADRs and HFRs. In these embodiments, the system 100 may include a DFR 106 and/or a DSR 108 to accommodate the multiple ADRs and HFRs. As shown in FIG. 4, for example, the system 100 may include two or more ADRs. The second ADR 120 may allow additional processing downstream of the HFR 104. In these embodiments, the HFR 104 may receive digestate from the first ADR 102, as discussed above; however, instead of transferring the H/F products back to the first ADR 102, as shown in FIGS. 1-3 for example, the H/F products from the HFR 104 are instead transferred to the second ADR 120, as shown in FIG. 4. The second ADR 120 may digest the H/F products in a similar manner as discussed above with respect to the single ADR 102. Biogas produced by the second ADR 120 may combine with the first ADR 102 and flow to the biogas sub-system 110.

In embodiments with two ADRs, the environment for each ADR 102, 120 may be the same or different. For example, one ADR 102, 120 may have a thermophilic environment while the other ADR 120, 102 may have a mesophilic environment, or both 102, 120 may have a thermophilic or mesophilic environment. Embodiments with two ADRs may also include one or more of pretreatment of feedstock, recuperative thickening, ammonia removal, and/or solids separation of the HFR 104 contents, as discussed above with respect to the embodiment having a single ADR 102. While only two ADRs are depicted, it is contemplated that multiple ADRs, as well as multiple other receptacles described herein may be included in a system of the present disclosure.

Methods for Improving Anaerobic Digestion

Methods of the present disclosure include feeding a digestate to post-AD microorganisms and allowing the post-AD microorganisms to hydrolyze and ferment the digestate (e.g., recalcitrant materials in the digestate) and produce hydrolysis and fermentation products. Disclosed methods further include storing the post-AD microorganisms in an environment having conditions that are selected for improved growth of the post-AD microorganisms. For example, the controlled environmental conditions may include temperature, pH, nutrients, acids, alkalinity, ammonia, and the like. For example, the method may include establishing a thermophilic anaerobic digestion (TAD) or mesophilic anaerobic digestion (MAD) system according to known methods. For example, the post-AD microorganisms may be stored in an HFR 104, as described above. As one example, the post-AD microorganisms may be activated from a frozen stored state or obtained from another HFR 104 containing the post-AD microorganisms. In preparation for inoculation, a nutrient solution, specific for each microorganism, may be added to the HFR 104 and brought to temperature (e.g., 75° C.). The HFR 104 may then be inoculated with a seed containing the post-AD microorganism (e.g., *C. bescii*). The microbial population may be estimated, for example, based on its capacity to produce acetate. Based on the estimated microbial population, the HFR 104 may be fed the appropriate amount of digestate according to an assumed food to microorganism (F:M) ratio. The F:M ratio can be determined by dividing the mass of food (e.g., cellulose and recalcitrant biomass) by the mass of microorganisms. The post-AD microorganisms may be allowed time to hydrolyze and ferment the digestate into H/F products. The amount of time for hydrolysis (i.e., solids retention time) may be determined by VSR. The VSR is an indication of hydrolysis and conversion of cellulose and recalcitrant biomass into soluble acids.

In some embodiments, the method may include feeding the H/F products to AD microorganisms to produce additional biogas. In these embodiments, the method may further include storing the AD microorganisms in an environment having conditions that are selected for improved growth of the AD microorganisms. For example, the controlled environmental conditions may include temperature, pH, nutrients, acids, alkalinity, ammonia, and the like. For example, the method may include establishing a thermophilic anaerobic digestion (TAD) or mesophilic anaerobic digestion (MAD) system according to known methods. For example, the AD microorganisms may be stored in an ADR 102, as described above.

The digestate fed to the post-AD microorganisms is a product of anaerobic digestion. For example, disclosed methods may include feeding or introducing a feedstock to AD microorganisms and allowing the AD microorganisms to digest the feedstock and produce biogas and digestate. In these embodiments, the method may further include creating an environment having conditions that are selected for improved growth of the AD microorganisms, and storing the AD microorganisms in such an environment. For example, the controlled environmental conditions may include temperature, pH, nutrients, acids, alkalinity, ammonia, and the like. For example, the method may include establishing a thermophilic anaerobic digestion (TAD) or mesophilic anaerobic digestion (MAD) system according to known methods. For example, the AD microorganisms may be stored in an ADR, as described above.

In some embodiments, before feeding the feedstock to AD microorganisms, the method may include processing the feedstock with a pretreatment process to facilitate digestion by the AD microorganisms. For example, the pretreatment process may include biological hydrolysis (e.g., acid phase, enzymatic hydrolysis, etc.), mechanical hydrolysis, acid hydrolysis, thermal hydrolysis, thermal/chemical hydrolysis, pretreatment *C. bescii* hydrolysis, or other known pretreatment processes. As one example, pretreatment processes may include pre-digestion dewatering, thermal hydrolysis, and hydrolyzed/fermented sludge fed to the HFR 104, as shown in FIG. 5.

In some embodiments, the method may include recuperative thickening of the post-AD microorganisms. For example, solids separation for recuperative thickening can be accomplished with conventional thickening equipment such as centrifuges and rotary drum thickeners that can limit the exposure to air.

In some embodiments, the method may include ammonia stripping of the hydrolysis and fermentation effluent. For example, the method may include increasing the pH and temperature of the hydrolysis and fermentation effluent to reduce the ammonia concentration. As one example, the method may include increasing the pH by adding a base or alkali to the hydrolysis and fermentation effluent.

In some embodiments, the method may include acid scrubbing the ammonia reduced effluent. For example, the method may include flowing the ammonia reduced effluent through an acid scrubber to further eliminate the ammonia from the liquid.

In some embodiments, the method may include feeding the ammonia reduced hydrolysis and fermentation effluent to the AD microorganisms to produce ammonia reduced digestate. The method may include feeding the ammonia reduced digestate to the post-AD microorganisms to hydrolyze and ferment into H/F products.

In some embodiments, the method may include monitoring parameters of the post-AD microorganisms and their environment and/or the AD microorganisms and their environment and determining any changes in parameters. For example, monitored parameters for the post-AD microorganisms and their environment may include post-AD microorganism concentration, post-AD microorganisms growth rate, temperature, pH, ammonia, acetate formation, volatile solids (VS) reduction, and the like. As another example, monitored parameters for the AD microorganisms and their environment may include VS concentration, temperature, biogas production, VS reduction, and the like. In these embodiments, the method may further include increasing or decreasing the feed rate based on the changes in parameters. The feed rate to the post-AD microorganisms (e.g., to the HFR 104) can be controlled by the flow rate of the digestate fed to the post-AD microorganisms (e.g., to the HFR 104). For example, the method may include increasing the feed rate to the post-AD microorganisms if the growth rate of the post-AD microorganisms increases. In these embodiments, the method may further include adjusting the circulation rate of the digestate from the AD microorganisms (ADR 102) to the post-AD microorganisms (HFR 104) and of the H/F products from the post-AD microorganisms (HFR 104) to the AD microorganisms (ADR 102). In these embodiments, increasing or decreasing the feed rate and/or adjusting the circulation rate may control the acids and alkalinity in the AD environment (e.g., ADR 102) and post-AD environment (e.g., HFR 104). In addition, in some embodiments, the method may include adding chemical alkalinity to control the acids and alkalinity in the AD environment (e.g., ADR 102) and post-AD environment (e.g., HFR 104).

EXAMPLES

Example 1: Anaerobic Digestion

In one experiment, conventional anaerobic digestion is used for anaerobic digestion of feedstock, without additional processing. In this experiment, a control digestion system is used to validate performance of anaerobic digestion alone, without additional processing. For example, the system is tested for loading rates, retention times, optimal temperature, optimal pH, amount of gas produced, amount of residual biosolids, impact on digestate odor, impact on dewatering, and the like.

Example 2: Anaerobic Digestion with Post-Anaerobic Digestion Processing

In another experiment, conventional anaerobic digestion is used for anaerobic digestion of feedstock and one or more microorganisms described herein are used in post-anaerobic digestion processing. In this experiment, an experimental digestion system is used to validate performance of anaerobic digestion when combined with post-anaerobic digestion processing as disclosed herein. For example, the system is tested for loading rates, retention times, optimal temperature, optimal pH, amount of gas produced, amount of residual biosolids, impact on odor, impact on dewatering, and the like. The test results are compared to the control to assess performance improvement.

Example 3: Anaerobic Digestion with Post- and Pre-Anaerobic Digestion Processing In another experiment, conventional anaerobic digestion is used for anaerobic digestion with one or more microorganisms described herein used for post-anaerobic digestion processing and pre-anaerobic digestion treatment. In this experiment, an experimental digestion system is used to validate performance of anaerobic digestion when combined with post-anaerobic digestion processing and pre-anaerobic digestion treatment as disclosed herein. For example, the system is tested for loading rates, retention times, optimal temperature, optimal pH, amount of gas produced, amount of residual biosolids, impact on digestate odor, impact on dewatering, and the like. The test results are compared to the control and to the experiment without post-anaerobic digestion treatment to assess performance improvement.

While multiple embodiments are disclosed, still other embodiments of the present invention will become apparent to those skilled in the art from the following detailed description. As will be apparent, the invention is capable of modifications in various aspects, all without departing from the spirit and scope of the present invention. Accordingly, the detailed description is to be regarded as illustrative in nature and not restrictive.

Although the present disclosure has been described with a certain degree of particularity, it is understood the disclosure has been made by way of example, and changes in detail or structure may be made without departing from the spirit of the disclosure as defined in the appended claims.

What is claimed is:

1. A post-anaerobic digestion process for increasing an amount of biogas produced during anaerobic digestion, comprising:
    introducing a feedstock to a first plurality of anaerobic microorganisms in a first receptacle, wherein the first plurality of anaerobic microorganisms convert the feedstock into primary digested sludge and biogas;
    introducing, downstream from the first receptacle, the primary digested sludge to a second plurality of anaerobic microorganisms in a second receptacle separate from the first receptacle, wherein the second plurality of anaerobic microorganisms hydrolyze the primary digested sludge into hydrolyzed sludge; and
    introducing, downstream from the second receptacle, the hydrolyzed sludge to a third plurality of anaerobic microorganisms in a third receptacle separate from at least one of the first receptacle and the second receptacle, wherein the third plurality of anaerobic microorganisms digest the hydrolyzed sludge to produce secondary digested sludge and biogas.

2. The post-anaerobic digestion process of claim 1, wherein the feedstock is a product of anaerobic digestion.

3. The post-anaerobic digestion process of claim 1, wherein the second plurality of anaerobic microorganisms comprise thermophilic bacteria.

4. The post-anaerobic digestion process of claim 3, wherein the thermophilic bacteria comprise one or more bacteria selected from the genus *Caldicellulosiruptor*, *Clostridium thermocellum*, and *Thermoanaerobacterium saccharolyticum*.

5. The post-anaerobic digestion process of claim 3, wherein the thermophilic bacteria is *Caldicellulosiruptor bescii* (*C. bescii*).

6. The post-anaerobic digestion process of claim 1, further comprising allowing the first plurality of anaerobic microorganisms to hydrolyze one or more recalcitrant materials in the feedstock.

7. The post-anaerobic digestion process of claim 6, wherein the one or more recalcitrant materials comprise cellulosic material.

8. The post-anaerobic digestion process of claim 1, further comprising storing the second plurality of anaerobic microorganisms in an environment having mesophilic or thermophilic temperatures.

9. The post-anaerobic digestion process of claim 1, wherein the second plurality of anaerobic microorganisms comprise methanogens.

10. The post-anaerobic digestion process of claim 1, wherein the introducing the primary digested sludge to the second plurality of anaerobic microorganisms comprises passing the primary digested sludge from the first receptacle to the second receptacle via fluid conduit.

11. The post-anaerobic digestion process of claim 1, wherein the third receptacle is separate from both the first receptacle and the second receptacle.

12. The post-anaerobic digestion process of claim 1, wherein the feedstock is municipal organic waste.

13. A post-anaerobic digestion process for increasing an amount of biogas produced during anaerobic digestion, comprising:
- introducing organic material to a first plurality of anaerobic microorganisms in a first receptacle, wherein the first plurality of anaerobic microorganisms convert the organic material into biogas and biosolids;
- feeding the biosolids to a second plurality of anaerobic microorganisms in a second receptacle separate from the first receptacle, wherein the second plurality of anaerobic microorganisms convert the biosolids into hydrolysis products; and
- feeding the hydrolysis products directly to the first plurality of anaerobic microorganisms in the first receptacle for conversion into additional biogas.

\* \* \* \* \*